United States Patent [19]

O'Doherty

[11] 3,941,882

[45] Mar. 2, 1976

[54] RODENTICIDAL IMIDAZO-PYRIDINES

[75] Inventor: George O. P. O'Doherty, Greenfield, Ind.

[73] Assignee: Eli Lilly and Company, Indianapolis, Ind.

[22] Filed: Oct. 23, 1974

[21] Appl. No.: 517,265

Related U.S. Application Data

[63] Continuation-in-part of Ser. No. 498,341, Aug. 19, 1974, abandoned, which is a continuation-in-part of Ser. No. 416,338, Nov. 15, 1973, abandoned.

[52] U.S. Cl.................................. 424/263; 424/84
[51] Int. Cl.².................... A01N 9/22; A01N 17/14

[58] Field of Search............................... 424/84, 263

[56] References Cited

UNITED STATES PATENTS 3,561,948   2/1971   Dealtry et al................... 71/92

*Primary Examiner*—V. D. Turner
*Attorney, Agent, or Firm*—Kathleen R. S. Page; Everet F. Smith

[57] ABSTRACT

Certain substituted-2-fluoroalkyl-1H-imidazo(4,5-b)-pyridines as rodenticides.

16 Claims, No Drawings

RODENTICIDAL IMIDAZO-PYRIDINES

CROSS-REFERENCE TO RELATED APPLICATION

This is a continuation-in-part of my copending application Ser. No. 498,341, filed Aug. 19, 1974 and abandoned after the filing of this application. Application Ser. No. 498,341 was in turn a continuation-in-part of my then copending application Ser. NO. 416,338, filed Nov. 15, 1973 and abandoned after the filing of application Ser. No. 498,341.

SUMMARY OF THE INVENTION

The present invention is directed to methods employing and compositions comprising certain compounds as rodenticides. These are compounds of the following formula

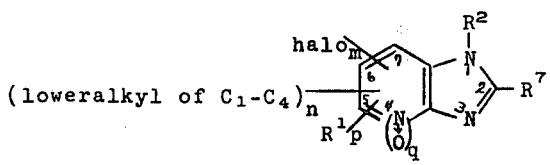

and the salts, with non-toxic cations, of those compounds wherein $R^2$ represents hydrogen or hydroxy; wherein $R^1$ represents
  1. $-CF_3$,
  2. $-CF_2Cl$, or
  3. $-CF_2H$;

$m$ represents an integer from 0 to 3; $q$ represents 0 or 1; each of $n$ and $p$ represents 0 or 1, subject to the limitations (1) that where $n$ is 1, the loweralkyl group so specified is at the 6-position; and (2) that the sum of $m$, $n$, and $p$ is an integer from 1 to 3;

$R^2$ represents
  1. hydrogen,
  2. hydroxy, or
  3. $OR^3$ wherein $R^3$ represents
     a. alkyl of $C_1$-$C_8$,
     b. (loweralkoxy of $C_1$-$C_4$)methyl,
     c. alkenyl of $C_2$-$C_8$,
     d. cycloalkyl of $C_5$-$C_6$,
     e. benzyl,
     f. phenethyl,
     g. alkanoyl of $C_2$-$C_{18}$,
     h. alkenoyl of $C_3$-$C_{18}$,
     i. carbamoyl of the formula

wherein one $R^4$ represents phenyl, loweralkyl of $C_1$-$C_4$, or loweralkenyl of $C_2$-$C_4$, and the lower $R^4$ represents hydrogen, loweralkyl of $C_1$-$C_4$, or loweralkenyl of $C_2$-$C_4$, subject to the limitation that both $R^4$ moieties taken together do not contain more than six carbon atoms;
     j. radical of the formula

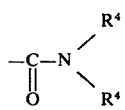

loweralkyl of $C_1$-$C_4$ or

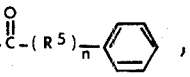

k. radical of the formula

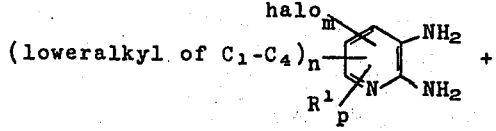

wherein $R^5$ represents methylene, ethylene, or vinylene, and $n$ represents 0 or 1,
     l. $-SO_2-R^6$ wherein $R^6$ is loweralkyl as above defined, cycloalkyl of $C_5$-$C_6$, phenyl, benzyl, or phenyl bearing from 1–3 substituents, each of which is independently amino, nitro, chloro, methyl, or methoxy;
and $R^7$ represents
  1. perfluoroalkyl of $C_1$-$C_7$,
  2. $-CF_2H$, or
  3. $-CF_2-CF_2H$.

DETAILED DESCRIPTION OF THE INVENTION

The compounds to be employed in accordance with the present invention are prepared in conventional procedures. Those compounds in which the 1-substituent ($R^2$) is hydrogen are prepared by condensing the respective pyridinediamine with an acid comprising the desired 2-position moiety:

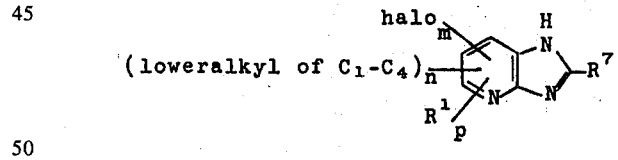

$$HO-\overset{O}{\underset{\|}{C}}-R^7 \longrightarrow$$

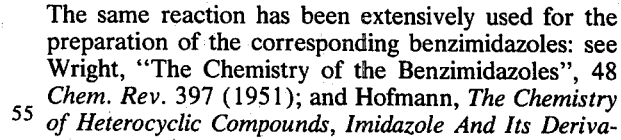

The same reaction has been extensively used for the preparation of the corresponding benzimidazoles: see Wright, "The Chemistry of the Benzimidazoles", 48 Chem. Rev. 397 (1951); and Hofmann, The Chemistry of Heterocyclic Compounds, Imidazole And Its Derivatives, Part I (Interscience Publishers, Inc., N.Y.). The reaction is conducted in like manner for the preparation of the present imidazopyridines. See also U.S. Pat. Nos. 3,459,759 and 3,681,369; and copending applications 181,574 and 236,195 (and corresponding Belgian Pat. No. 764,591, granted Sept. 20, 1971, or corresponding South African Pat. No. 1481/71, granted Mar. 1, 1972). Application 181,574 was issued May 28, 1974 as Pat. No. 3,813,408; application 236,195 was issued June 18, 1974 as Pat. No. 3,818,022.

Those compounds in which the 1-position substituent is any candidate moiety other than hydrogen are prepared by an alternative route. In this route, a nitroaminopyridine is acylated with an acyl group comprising the desired $R^7$ moiety, and the resulting nitroamide is hydrogenated, preferably in the presence of a catalytic amount of palladium or platinum.

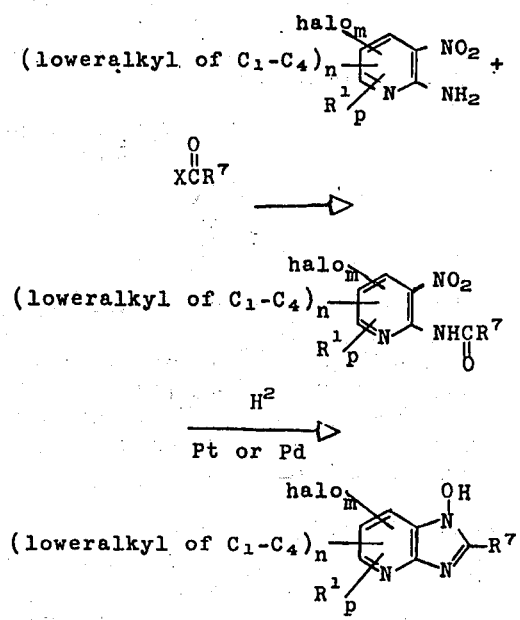

The reaction, which results in the preparation of the corresponding 1-hydroxyimidazopyridine, is described in detail in copending application Ser. No. 181,574. The 1-hydroxycompounds are then reacted with a halide, in the presence of base to serve as hydrogen halide acceptor, to convert the 1-hydroxy compounds to the corresponding 1-O-$R^3$ compounds. This reaction and alternative reactions for the preparation of the 1-O-$R^3$ compounds are described in more detail in copending application Ser. No. 236,195. As noted above, applications 181,574 and 236,195 correspond to Belgian patent 764,591, and South African Pat. No. 1481/71, more fully described above.

In the compounds the preparation of which is described in applications 181,574 and 236,195, the substituents on the pyridine ring are variously defined but do not include the loweralkyl substituent set forth above. However, such compounds are prepared in the same procedures, using appropriately substituted starting materials. For the preparation of starting materials, generally, see Klingsberg, *The Chemistry of Heterocyclic Compounds, Pyridine And Derivatives*, Parts 1–4 (Interscience Publishers, Inc., New York, 1960–1964); and Elderfield, *Heterocyclic Compounds* (Wiley, New York, 1950–67), especially Vol. 1.

In those of the compounds wherein $R^2$ represents hydrogen or hydroxy, the proton is acidic and accordingly the compounds form salts with cations. The identity of the cation is not critical. However, it is generally preferred that the cation be non-toxic, that is, that the toxicity of the resulting salt not be significantly different from that of the compound per se. While the objective of a rodenticide is the killing of rodents, such killing must be achieved with a certain mode of action. As discussed below, a salt-forming moiety which contributes any significant toxicity is undesirable because it may interfere with the unique mode of action and render the compound less suitable for rodenticidal use.

Suitable salts are those with alkali metals, such as sodium, potassium, lithium, cesium, and rubidium; alkaline earth metals, such as calcium and strontium; and organic amines. While the identity of the organic amine is not critical, preferred organic amines are those which have relatively high base strength, such as a dissociation constant ($K_b$) of the order of $10^{-5}$ or greater. In general, the alkylamines, cycloalkylamines, alkylenepolyamines, and aralkylamines are classes of compounds exhibiting adequate base strengths. Thus, representative bases include methylamine, dimethylamine, trimethylamine, methyldiethylamine, ethylamine, diethylamine, triethylamine, n-propylamine, di-n-propylamine, tri-n-propylamine, n-amylamine, cyclohexylamine, piperidine, pyrrolidine, N-methylpyrrolidine, diisopropylamine, ethylenediamine, tetramethylenediamine, ethanolamine, benzylamine, isobutylamine, di-n-butylamine, and the like.

The $N^4$-oxides ($q = 1$) are prepared in conventional procedures: see U.S. Pat. No. 3,459,759.

Representative compounds to be employed in accordance with the present invention include the following:
1-methoxy-6-chloro-2-heptafluoro-n-propyl-1H-imidazo(4,5-b)-pyridine, m.p. 48°–50°C.
1-methoxy-6-bromo-2-heptafluoro-n-propyl-1H-imidazo(4,5-b)pyridine m.p. 71°–73°C.
6-chloro-2-pentafluoroethyl-1H-imidazo(4,5-b)pyridine, m.p. 239°–240°C.
1-methoxy-6-chloro-2-heptafluoroisopropyl-1H-imidazo(4,5-b)pyridine m.p. 46°–48°C.
1-methoxy-6-chloro-2-trifluoromethyl-1H-imidazo(4,5-b)pyridine, m.p. 91°–92°C.
1-methoxy-6-chloro-2-pentafluoroethyl-1H-imidazo(4,5-b)pyridine, m.p. 61°–63°C.
1-ethoxy-6-chloro-2-trifluoromethyl-1H-imidazo(4,5-b)pyridine, $n_D^{25} = 1.5082$.
1-isopropoxy-6-chloro-2-trifluoromethyl-1H-imidazo(4,5-b)pyridine, m.p. 49°–51°C.
1-benzyloxy-6-chloro-2-trifluoromethyl-1H-imidazo(4,5-b)pyridine, m.p. 107°–109°C.
1-methylcarbamoyloxy-6-chloro-2-trifluoromethyl-1H-imidazo(4,5-b)pyridine, m.p. 267°C.
1-dimethylcarbamoyloxy-6-chloro-2-trifluoromethyl-1H-imidazo(4,5-b)pyridine, m.p. 134°–135°C.
1-acetoxy-6-chloro-2-trifluoromethyl-1H-imidazo(4,5-b)pyridine, m.p. 103°–104°C.
1-octanoyloxy-6-chloro-2-trifluoromethyl-1H-imidazo(4,5-b)pyridine, m.p. 33°–35°C.
1-hydroxy-6-methyl-2-trifluoromethyl-1H-imidazo(4,5-b)pyridine, m.p. 275°C.
1-hydroxy-2,6-bis(trifluoromethyl)-1H-imidazo(4,5-b)pyridine, m.p. 239°–240°C.
1-methoxy-2,6-bis(trifluoromethyl)-1H-imidazo(4,5-b)pyridine, m.p. 54°–55°C.
1-allylcarbamoyloxy-6-chloro-2-trifluoromethyl-1H-imidazo(4,5-b)pyridine, m.p. 210°C.
1-hydroxy-6-chloro-2-heptafluoro-n-propyl-1H-imidazo(4,5-b)pyridine, m.p. 249°C.
1-hydroxy-6-bromo-2-trifluoromethyl-1H-imidazo(4,5-b)pyridine, m.p. 256°–258°C.
1-hydroxy-6-chloro-2-pentafluoroethyl-1H-imidazo(4,5-b)pyridine, m.p. 240°–242°C.
1-allyloxy-6-chloro-2-trifluoromethyl-1H-imidazo(4,5-b)pyridine, $n_D^{25} = 1.5204$
1-hydroxy-6-chloro-2-trifluoromethyl-1H-imidazo(4,5-b)pyridine, m.p. 268°–270°C.
1-(phenoxycarbonyloxy)-6-chloro-2-trifluoromethyl-1H-imidazo(4,5-b)pyridine, m.p. 125°–126°C.
1-palmitoyloxy-6-chloro-2-trifluoromethyl-1H-imidazo(4,5-b)pyridine, m.p. 64°–65°C.
1-hydroxy-6-chloro-2-difluoromethyl-1H-imidazo(4,5-b)pyridine, m.p. 252°–253°C.
1-methoxycarbonyloxy-6-chloro-2-trifluoromethyl-1H-imidazo(4,5-b)pyridine, m.p. 115°–116°C.
1-hydroxy-6-chloro-2-perfluoro-n-heptyl-1H-imidazo(4,5-b)pyridine, m.p. 230°–235°C.

1-stearoyloxy-6-chloro-2-trifluoromethyl-1H-imidazo(4,5-b)pyridine, m.p. 68°–70°C.
1-cyclohexyloxy-6-chloro-2-trifluoromethyl-1H-imidazo(4,5-b)pyridine, m.p. 66°–68°C.
1n-heptyloxy-6-chloro-2-trifluoromethyl-1H-imidazo(4,5-b)pyridine, $n_D^{25}$ = 1.5012.
1-hydroxy-6-chloro-2-(1,1,2,2-tetrafluoroethyl)-1H-imidazo(4,5-b)pyridine, m.p. 213°–214°C.
1-acryloyloxy-6-chloro-2-trifluoromethyl-1H-imidazo(4,5-b)pyridine, m.p. 94°–95°C.
1-ethoxy-2,6-bis(trifluoromethyl)-1H-imidazo(4,5-b)pyridine, $n_D^{25}$ = 1.5620.
1-(isopropoxycarbonyloxy)-6-chloro-2-trifluoromethyl-1H-imidazo(4,5-b)pyridine, m.p. 120°–122°C.
1-benzyloxy-6-chloro-2-trifluoromethyl-1H-imidazo(4,5-b)pyridine, m.p. 135°–136°C.
1-cinnamoyloxy-6-chloro-2-trifluoromethyl-1H-imidazo(4,5-b)pyridine, m.p. 132°–133°C.
1-hydroxy-6-chloro-2-heptafluoro-n-propyl-1H-imidazo(4,5-b)pyridine, m.p. 248°–251°C.
1-methylsulfonyloxy-6-chloro-2-trifluoromethyl-1H-imidazo(4,5-b)pyridine
6-chloro-2-trifluoromethyl-1H-imidazo(4,5-b)pyridine, m.p. 292°–294°C.
6-bromo-2-trifluoromethyl-1H-imidazo(4,5-b)pyridine, m.p. 280°C.
2,6-bis(trifluoromethyl)-1H-imidazo(4,5-b)pyridine, m.p. 104°–106°C.
6-chloro-2-(1,1,2,2-tetrafluoroethyl)-1H-imidazo(4,5-b)pyridine, m.p. 238°–239°C.
1-hydroxy-6-chloro-2-trifluoromethyl-1H-imidazo(4,5-b)pyridine triethylamine salt; NMR (in deuterium oxide) showed a triplet centered at 82 cps (9H); a quartet centered at 196 cps (6H); a meta-coupled doublet at 400 cps (1H); and a second meta-coupled doublet centered at 503 cps (1H).
1-hydroxy-6-chloro-2-trifluoromethyl-1H-imidazo(4,5-b)pyridine benzylamine salt, m.p. 200°–202°C.
6-chloro-2-trifluoromethyl-1H-imidazo(4,5-b)pyridine, sodium salt.
2,6-bis(trifluoromethyl)-1H-imidazo(4,5-b)pyridine, calcium salt.
1-hydroxy-6-chloro-2-pentafluoroethyl-1H-imidazo(4,5-b)pyridine, potassium salt.
5-chloro-2,6-bis(trifluoromethyl)-1H-imidazo(4,5-b)pyridine, m.p. 190°C. with sublimation from 180°C.
5,6-dichloro-2-perfluoro-n-propyl-1H-imidazo(4,5-b)pyridine, 4-oxide, m.p. 264°–265.5°C.
5,6,7-trichloro-2-perfluoro-n-propyl-1H-imidazo(4,5-b)pyridine, m.p. 161°–163°C.
1-methoxy-5,6-dichloro-2-trifluoromethyl-1H-imidazo(4,5-b)pyridine, 4-oxide, m.p. 218°–220°C.
1-methoxy-5,6,7-trichloro-2-trifluoromethyl-1H-imidazo(4,5-b)pyridine, m.p. 138°–140°C.
1-methoxy-6-chloro-2-trifluoromethyl-1H-imidazo(4,5-b)pyridine, 4-oxide, m.p. 218°–220°C.
1-methylcarbamoyloxy-6-chloro-2-(1,1,2,2-tetrafluoroethyl)-1H-imidazo(4,5-b)pyridine, m.p. 225°–227°C.
1-pivaloyloxy-6-chloro-2-trifluoromethyl-1H-imidazo(4,5-b)pyridine, m.p. 54°–58°C.
5,6,7-trichloro-2-(1,1,2,2-tetrafluoroethyl)-1H-imidazo(4,5-b)pyridine.
1-allyloxy-5,6,7-trichloro-2-(1,1,2,2-tetrafluoroethyl)-1H-imidazo(4,5-b)pyridine.

Preferred compounds are those wherein the substituents or the pyridine ring are halo, methyl, or $CF_3$, subject to the restrictions stated above; or those wherein $R^2$ represents hydrogen, hydroxy or $-OR^3$ wherein $R^3$ is loweralkyl of $C_1$-$C_4$, cyclohexyl, benzyl, carbamoyl bearing at least one loweralkyl of $C_1$-$C_4$ or lower alkenyl of $C_2$-$C_4$ (subject to the already-stated limitation that both substituents taken together do not contain more than six atoms), loweralkoxy of $C_1$-$C_4$ carbonyl, phenoxycarbonyl, cinnamoyl, or benzoyl. Even more preferred are those of the compounds to which both of the above restrictions apply. Preferred halo substituents are bromo, chloro, and fluoro; most preferred is chloro.

The rodenticidal agents of the present invention can be used in the same ways in which known rodenticidal agents are used. Fundamentally, the present invention is directed to a method for limiting or eradicating a rodent population which comprises supplying to a locus frequented by said population an effective, rodenticidal, amount of the present active agent.

The term "rodent" refers most broadly to an animal of the class Mammalia, order Rodentia. The present invention is useful for the control of rodents in this broad sense. However, many rodents are beneficial, or at least are not undesirable. The rodents which are generally undesirable are of the families Muridae and Cricetidae. The family Muridae includes such species as the house mouse (*Mus musculus*), the Norway (or brown or common) rat (*Rattus norvegicus*), and *Rattus rattus*, of which there are several sub-species: the black rat (*R. r. rattus*), the roof rat (*R. r. frugivorus*), and *R. r. alexandrinus*. The family Cricetidae includes such species as the white-footed (or deer) mouse (*Peromyscus leucopus*), the pack rat (e.g., *Neotoma cinerea*), and the meadow mouse (e.g., *Microtus pennsylvanicus*).

Since rodents are known to be capable of perceiving a relationship between food intake and any subsequent deleterious effect, a preferred characteristic of a rodenticide is that it have only a delayed toxic effect. The compounds to be employed in accordance with the present invention, with proper selection of doses, exhibit such effect. Moreover, the present compounds exhibit this delayed toxic effect over a wide range of doses. Therefore, while the present active agent can be supplied in an amount large enough to cause a relatively prompt toxic effect from a single feeding, it is generally preferred to supply the active agent in an amount which is not acutely lethal in any single feeding but merely contributes to a cumulative lethal effect. Accordingly, it is preferred that the active agent be supplied for a period of time sufficient for at least two feedings, and preferably for three or more feedings. Hence, in a preferred embodiment, the present method is a method for limiting or eradicating a rodent population which comprises supplying to a locus frequented by said population, during a period of time sufficient for at least two feedings, an amount of the present active agent which is not acutely lethal upon a single feeding but which contributes to a cumulative lethal effect upon two or more feedings.

All of the compounds serving as the present active agent admit of dosing with an effective, rodenticidal, amount. The precise amount which will constitute an effective amount varies with the particular compound, the particular rodent, whether an acute or cumulative effect is desired, and other factors. Larger amounts may be required for compounds employed as salts with high-molecular weight salt-forming moieties. Also, it is believed that all 1-$OR^3$ groups convert to either the 1-H or 1-OH so that the identity of the $R^3$ group is not critical. However, it functions as a diluent and larger amounts may be needed to supply an effective amount of the active moiety when the $R^3$ group is bulky.

The present invention can be carried out with a single member of the genus as herein defined. However, as those skilled in the art will understand, the invention can also be practiced with a mixture of two or more members of the genus defined herein. In such practice, the amount of each member to be employed can be reduced accordingly so that the active agent in toto constitutes an effective amount.

Although the active agent is effective when administered by any route, the nature of rodent populations is such that only oral ingestion is practical. Furthermore, although the active agent can be administered alone, again the nature of rodent populations is such that it is preferred to supply the present active agent in a formulation comprising the active agent. Therefore, a preferred embodiment of the present invention is a composition comprising the active agent in an effective, rodenticidal, concentration. Typically, concentrations of the present active agent from 5 to 2000 ppm (parts by weight of active agent per million parts by weight of finished composition) have been found to be effective.

Suitable compositions are prepared in conventional procedures with one or more conventional adjuvants. In the case of solid compositions, the active agent can be formulated with inert substances such as talc, chalk, and the like; nutritive substances such as oatmeal, ground corn, corn oil, ground oats, soybean products, wheat products, dried skimmed milk, animal fat, salts such as calcium carbonate, dicalcium phosphate, and sodium chloride; trace minerals such as manganese sulfate, zinc carbonate, ferrous sulfate, copper oxide, potassium iodide, and calcium carbonate; vitamins; and sweetening substances such as sugar, molasses, honey, and artificial sweeteners. Suitable adjuvants also include those substances recognized by rodents as attractants--including not only nutritive substances but also sex hormones and the like. Solid compositions can be offered in finely divided form or compacted as pellets or granules. For liquid administration, the compounds can be formulated in water intended to serve as drinking water. A given compound can be converted to a salt, to achieve water solubility, or a surface active dispersing agent can be used. Where the compounds are formulated with only an inert carrier, such composition can be employed as a "tracking powder"; such a powder is dusted on a surface over which rodents walk, so that the rodents consume the composition when they clean themselves. Preferred adjuvants are those which are nutritive substances, especially grain and grain products, and attractants.

The compounds serving as the present active agent apparently act by different modes of action. Those compounds bearing a single substituent located at the 6-position are believed to be operative through a mechanism of anti-coagulation; experiments to date show that these compounds antagonize the vitamin K-dependent factors necessary to coagulation. The remainder of the compounds serving as active agent apparently do not share the anticoagulant mechanism but the precise mechanism of these compounds is not understood.

The following examples illustrate the present invention and will enable those skilled in the art to practice the same.

EXAMPLE 1

A quantity of a standard animal feed of the following composition:

| Ingredients | Percent | Lbs./Ton |
|---|---|---|
| Corn, Yellow, Ground | 42.275 | 845.5 |
| Oats, Ground | 10.0 | 200.0 |
| Wheat Middlings | 10.0 | 200.0 |
| Soybean Oil Meal, Solvent Extracted Dehulled, 50 % | 18.0 | 360.0 |
| Skimmed Milk, Dried | 5.0 | 100.0 |
| Corn, Distillers Dried Solubles | 2.5 | 50.0 |
| Alfalfa Meal, Dehydrated, 17 % | 2.5 | 50.0 |
| Whey, Whole Dried | 1.0 | 20.0 |
| Fish Meal with Solubles | 4.0 | 80.0 |
| Animal Fat, Beef Tallow | 2.0 | 40.0 |
| Dicalcium Phosphate, Feed Grade | 0.5 | 10.0 |
| Calcium Carbonate | 1.0 | 20.0 |
| Salt | 0.3 | 6.0 |
| Trace Mineral Premix AN-03 | 0.2 | 4.0 |
| Vitamin Premix CK-1 | 0.5 | 10.0 |
| Vitamin E Premix | 0.1 | 2.0 |
| Methionine Hydroxy Analog (HYDAN) | 0.125 | 2.5 |
| Total | 100.00 | 2000.0 | was divided into two portions. To each portion, there was added an amount of 1-methoxy-6-chloro-2-heptafluoro-n-propyl-1H-imidazo(4,5-b)pyridine, so that one portion contained 800 ppm of the compound, and the other portion contained 200 ppm of the compound.

Other modified feeds were prepared as described above but containing, in lieu of the compound identified above, 1-methoxy-6-bromo-2-heptafluoro-n-propyl-1H-imidazo(4,5-b)pyridine, 6-chloro-2-pentafluoroethyl-1H-imidazo(4,5-)pyridine, or 1-methoxy-6-chloro-2-heptafluoroisopropyl-1H-imidazo(4,5-b)pyridine, in the same or other concentrations.

EXAMPLES 2–28

Representative compounds were evaluated for rodenticidal effect in rats (*Rattus norvegicus*, Spraque-Dawley albino strain, male, each weighing 50–60 grams). Each compound to be evaluated was formulated as described in Example 1. Control rats were maintained on the standard animal feed described in Example 1. Control rats and rats to be treated were randomly assigned. Each group contained 5 or 6 rats. Feeding of the respective diet was ad libitum. Consumption per rat per day was checked, except on weekend days, and the rats were weighed and usually necropsied at death or termination of the experiment (generally, day 10).

The results were as reported in Table I, using the immediately following code:

NGP — no gross pathology
AH — abdominal hemorrhage
IH — intestinal hemorrhage
SIH — slight intestinal hemorrhage
LH or TH — lung (thoracic) hemorrhage
RI — redness in intestine
SRI — slight redness in intestine
NN — not necropsied
X — died
S — sacrificed
W — feed wastage
NH — nose hemorrhage
Test. H — testicular hemorrhage
SH — subcutaneous hemorrhage In the evaluation of several of the compounds, the rats were observed closely to determine the day of death.

Death occurred on the day marked by "X"; where no "X" is marked, the rat was found dead on the morning following the last indicated feeding. For the remaining compounds, no such close observation was made, and the rat was found dead on the morning following the last indicated feeding. Generally, the rats were not observed or feed consumption determined on weekend days.

In summary, the results reported in Table I show that none of the rats died of acute toxicity; and that essentially none of the rats survived the ten-day test period. Each succumbed of sub-acute toxicity, variously on the second through tenth day.

TABLE I

| Compound | Concentration of compound in diet | Grams of Feed Consumed per day of experiment | | | | | | | | | | Total feed consumed | Weight Change in grams | Necropsy Results |
|---|---|---|---|---|---|---|---|---|---|---|---|---|---|---|
| | | 1 | 2 | 3 | 4 | 5 | 6 | 7 | 8 | 9 | 10 | | | |
| 1-methoxy-6-chloro-2-heptafluoro-n-propyl-1H-imidazo-(4,5-b)pyridine | 800 | 8 | 10 | 8 | 9 | 7X | — | — | — | — | — | 42 | +5 | IH |
| | | 7 | 9 | 7 | 2X | — | — | — | — | — | — | 25 | +3 | LH |
| | | 6 | 9 | 6 | 5X | — | — | — | — | — | — | 26 | −1 | LH |
| | | 7 | 11 | 7 | 10 | 8X | — | — | — | — | — | 43 | +8 | bloody nose |
| | | 8 | 10 | 10 | 6 | 1X | — | — | — | — | — | 35 | +3 | LH |
| | | 4 | 8 | 7 | 7 | 7X | — | — | — | — | — | 33 | −3 | IH |
| | 200 | 8 | 9 | 8 | 9 | 14X | — | — | — | — | — | 48 | +10 | LH |
| | | 10 | 10 | 9 | 10 | 5X | — | — | — | — | — | 44 | +16 | bloody nose |
| | | 10 | 9 | 8 | 6X | — | — | — | — | — | — | 33 | +10 | LH |
| | | 10 | 11 | 8 | 12 | OX | — | — | — | — | — | 41 | +15 | SIH |
| | | 7 | 8 | 8 | 8 | 9 | 9 | 5 | 0 | 0 | X | 54 | — | NN |
| | | 11 | 11 | 12 | 6 | 10X | — | — | — | — | — | 50 | +13 | NGP |
| 1-methoxy-6-bromo-2-heptafluoro-n-propyl-1H-imidazo-(4,5-b)pyridine | 200 | 12 | 15 | — | — | 31 | — | — | — | — | — | 58 | +26 | LH |
| | | 11 | 11 | — | — | 30 | 1 | 1 | 0 | 0 | — | 54 | −7 | IH |
| | | 12 | 12 | — | — | 27 | 1 | 1 | — | — | — | 53 | +1 | LH |
| | | 14 | 13 | — | — | 39 | 14 | 8 | 11 | 10 | — | 109 | +33 | AH |
| | | 13 | 12 | — | — | 36 | 8 | 13 | 4 | 1 | — | 87 | +16 | LH, IH |
| 6-chloro-2-pentafluoroethyl-1H-imidazo(4,5-b)pyridine | 300 | 6 | 4 | 11 | — | — | 7 | — | — | — | — | 28 | −8 | IH |
| | | 8 | 7 | 8 | — | — | 33 | 5 | — | — | — | 61 | +1 | IH |
| | | 8 | 6 | 7 | — | — | 21 | — | — | — | — | 42 | −2 | IH |
| | | 8 | 7 | 8 | — | — | 27 | — | — | — | — | 50 | −9 | IH |
| | | 7 | 5 | 4 | 1 | — | — | — | — | — | — | 17 | −15 | IH |
| | 150 | 7 | 7 | 8 | — | — | 26 | — | — | — | — | 48 | +9 | NGP |
| | | 9 | 10 | 9 | — | 8 | — | — | — | — | — | 36 | +11 | IH |
| | | 6 | 5 | 6 | — | — | 14 | — | — | — | — | 31 | −2 | IH |
| | | 7 | 9 | 8 | — | 17 | — | — | — | — | — | 41 | +10 | SIH |
| | | 7 | 8 | 8 | — | — | 24 | — | — | — | — | 47 | +10 | NGP |
| 1-methoxy-6-chloro-2-heptafluoroisopropyl-1H-imidazo-(4,5-b)pyridine | 300 | 16 | 17 | 19 | 3 | — | — | — | — | — | — | 55 | +11 | TH |
| | | 20 | 22 | 20 | 15 | — | — | — | — | — | — | 77 | +12 | TH |
| | | 13 | 15 | 16 | 14 | 0 | 0 | 38 | — | — | — | 96 | +10 | AH, TH, SH |
| | | 17 | 18 | 17 | 16 | 1 | — | — | — | — | — | 69 | +14 | TH |
| | | 20 | 17 | 16 | 18 | 4 | — | — | — | — | — | 75 | +15 | TH, Test.H |
| | 200 | 14 | 17 | 17 | 16 | 9 | — | — | — | — | — | 73 | +12 | TH,SH, Test.H |
| | | 14 | 21 | 19 | 20 | 15 | — | — | — | — | — | 89 | +18 | TH, SH |
| | | 19 | 18 | 16 | 16 | — | 17 | — | — | — | — | 86 | +13 | TH, SH |
| | | 19 | 21 | 19 | 19 | 2 | — | — | — | — | — | 80 | +4 | TH |
| | | 17 | 15 | 15 | 18 | — | 11 | — | — | — | — | 76 | +3 | TH |
| 5,6-dichloro-2-(1,1,-2,2-tetrafluoroethyl)-1H-imidazo(4,5-b)pyridine | 100 (first test) | 10 | 10 | 6 | 8 | OX | — | — | — | — | — | 34 | −17 | NN |
| | | 11 | 13 | 7 | 12 | OX | — | — | — | — | — | 43 | −22 | NN |
| '' | 100 (second test) | 10 | 10 | 5X | — | — | — | — | — | — | — | 25 | −8 | NN |
| | | 6 | 6 | 6X | — | — | — | — | — | — | — | 18 | −2 | IH |
| | | 5 | 7 | 3X | — | — | — | — | — | — | — | 15 | −2 | IH |
| | | 6 | 5 | 5 | 1X | — | — | — | — | — | — | 17 | −3 | AH |
| | | 6 | 5 | 5X | — | — | — | — | — | — | — | W16 | −5 | AH |
| | | 5 | 7 | 3X | — | — | — | — | — | — | — | 15 | −2 | AH |
| '' | 50 | 4 | 7 | 7 | 9 | 10 | 8 | 7X | — | — | — | 52 | +7 | IH |
| | | 10 | 10 | 10 | 12 | 14 | 8 | 3X | — | — | — | 67 | +4 | IH |
| | | 7 | 10 | 9 | 10 | 9 | 8 | 7 | 2X | — | — | 62 | −3 | NGP |
| | | 6 | 8 | 7 | 9 | 9 | 8 | 10 | 1X | — | — | 58 | −5 | NGP |
| | | 7 | 7 | 9 | 8 | 10 | 6 | 7 | 3X | — | — | 57 | −2 | NGP |
| 5-fluoro-6-chloro-2-trifluoromethyl-1H-imidazo(4,5-b)pyridine | 100 (first test) | 12 | 9 | 5 | 10X | — | — | — | — | — | — | 36 | −12 | NN |
| | | 14 | 12 | 4X | — | — | — | — | — | — | — | 30 | −11 | NN |
| | | 10 | 10 | 2 | OX | — | — | — | — | — | — | 22 | −8 | NN |
| '' | 100 (second test) | 9 | 7 | 4 | 1X | — | — | — | — | — | — | 21 | −4 | AH |
| | | 6 | 5 | 5 | 2X | — | — | — | — | — | — | 18 | −7 | AH |
| | | 8 | 8 | 7 | 1X | — | — | — | — | — | — | 24 | −2 | AH |
| | | 9 | 8 | 7 | OX | — | — | — | — | — | — | 24 | 0 | AH |
| | | 7 | 6 | 5 | 3X | — | — | — | — | — | — | 21 | 6 | NGP |
| '' | 50 | 8 | 10 | 12 | 10 | 11 | 10 | 8 | 1X | — | — | 70 | +7 | IH |
| | | 6 | 7 | 9 | 7 | 10 | 7 | 4X | — | — | — | 50 | +4 | LH |
| | | 7 | 9 | 8 | 6 | 7 | 7 | 4X | — | — | — | 48 | −5 | IH |

TABLE I-continued

| Compound | Concentration of compound in diet | Grams of Feed Consumed per day of experiment | | | | | | | | | | Total feed consumed | Weight Change in grams | Necropsy Results |
|---|---|---|---|---|---|---|---|---|---|---|---|---|---|---|
| | | 1 | 2 | 3 | 4 | 5 | 6 | 7 | 8 | 9 | 10 | | | |
| | | 7 | 9 | 9 | 10 | 14 | 10 | 12 | 2X | — | — | 73 | +7 | NGP |
| | | 8 | 9 | 11 | 11 | 11 | 12 | 13 | 1X | — | — | 76 | +9 | IH |
| 5,6-dichloro-2-hepta-fluoro-n-propyl-1H-imidazo(4,5-b)pyridine | 50 | 13 | 12 | — | — | 23 | — | — | — | — | — | 48 | +2 | NGP |
| | | 12 | 12 | — | — | 29 | 3 | — | — | — | — | 56 | +1 | SIH |
| | | 12 | 8 | — | — | 23 | 3 | — | — | — | — | 46 | −5 | IH |
| | | 12 | 12 | — | — | 26 | — | — | — | — | — | 50 | +2 | IH |
| | | 12 | 10 | — | — | 17 | — | — | — | — | — | 39 | −2 | SIH |
| 1-methoxy-5,6-dichloro-2-heptafluoro-n-propyl-1H-imidazo(4,5-b)-pyridine | 100 | 13 | 13 | — | — | 26 | — | — | — | — | — | 52 | +11 | IH |
| | | 14 | 11 | — | — | 21 | — | — | — | — | — | 46 | +6 | IH |
| | | 9 | 8 | — | — | 19 | 1 | — | — | — | — | 37 | −9 | NGP |
| | | 12 | 12 | — | — | 18 | — | — | — | — | — | 42 | −2 | IH |
| | | 12 | 11 | — | — | 28 | — | — | — | — | — | 51 | +12 | IH |
| 5-bromo-6-chloro-2-trifluoromethyl-1H-imidazo(4,5-b)pyridine | 200 | 9 | 4 | 0 | — | — | — | — | — | — | — | 13 | −8 | IH |
| | | 7 | 4 | 0 | — | — | — | — | — | — | — | 11 | −9 | IH |
| | | 14 | 8 | 0 | — | — | — | — | — | — | — | 22 | −7 | IH |
| | | 11 | 4 | 4 | — | — | — | — | — | — | — | 19 | −16 | IH |
| | | 12 | 5 | — | — | — | — | — | — | — | — | 17 | −9 | IH |
| 5,6-dichloro-2-pentafluoroethyl-1H-imidazo-(4,5-b)pyridine | 50 | 11 | 9 | 10 | — | — | 23 | — | — | — | — | 53 | −1 | IH |
| | | 14 | 12 | 12 | — | — | 21 | — | — | — | — | 59 | +8 | IH |
| | | 13 | 12 | 12 | — | — | 31 | 0 | — | — | — | 68 | −3 | IH |
| | | 10 | 11 | 12 | — | — | 19 | — | — | — | — | 52 | −5 | IH |
| | | 13 | 12 | 12 | — | — | 37 | 2 | — | — | — | 76 | −3 | IH |
| " | 70 | 10 | 9 | 8 | — | 9 | — | — | — | — | — | 36 | −7 | IH |
| | | 8 | 12 | 9 | — | 8 | — | — | — | — | — | 37 | −3 | IH |
| | | 9 | 10 | 9 | — | 11 | — | — | — | — | — | 39 | −3 | IH |
| | | 7 | 9 | 6 | 1 | — | — | — | — | — | — | 23 | +1 | SIH |
| | | 11 | 11 | 11 | — | — | 21 | — | — | — | — | 54 | −4 | IH |
| 1-methoxy-5,6-dichloro-2-heptafluoro-n-propyl-1H-imidazo(4,5-b)-pyridine | 125 | 3 | 7 | 7 | — | 4 | — | — | — | — | — | 21 | −1 | IH |
| | | 11 | 11 | 9 | — | 9 | — | — | — | — | — | 40 | +1 | SIH |
| | | 8 | 9 | 7 | — | 10 | — | — | — | — | — | 34 | −4 | IH |
| | | 10 | 10 | 5 | 6 | — | — | — | — | — | — | 31 | +3 | SIH |
| | | 12 | 10 | 10 | — | — | 15 | — | — | — | — | 47 | +4 | NGP |
| " | 75 | 10 | 9 | 9 | — | — | 30 | 9 | 3 | — | — | 70 | +9 | IH |
| | | 11 | 10 | 8 | — | — | 32 | 10 | — | — | — | 71 | +12 | NGP |
| | | 8 | 8 | 7 | — | — | 28 | 4 | — | — | — | 55 | +4 | NGP |
| | | 8 | 7 | 7 | — | — | 24 | 3 | — | — | — | 49 | +6 | IH |
| | | 11 | 10 | 11 | — | — | 34 | 7 | — | — | — | 73 | +14 | NGP |
| 5,6-dichloro-2-trifluoromethyl-1H-imidazo(4,5-b)-pyridine | 100 | 10 | 7 | 6 | — | — | — | — | — | — | — | 23 | +1 | IH |
| | | 9 | 9 | 8 | 7 | — | — | — | — | — | — | 33 | −3 | IH |
| | | 16$^w$ | 10 | 7 | 3 | — | — | — | — | — | — | 36 | −2 | IH |
| | | 10 | 8 | 7 | 5 | — | — | — | — | — | — | 30 | −6 | IH |
| | | 9 | 10 | 9 | 8 | — | — | — | — | — | — | 36 | −1 | IH |
| " | 50 | 8 | 10 | 11 | 9 | — | — | 33 | 9 | — | — | 80 | +8 | IH |
| | | 10 | 11 | 11 | 9 | — | — | 41 | 14 | 13 | 13$^s$ | 122 | +13 | NGP |
| | | 9 | 9 | 9 | 9 | — | — | 29 | 7 | — | — | 72 | +5 | SIH |
| | | 7 | 9 | 9 | 9 | — | — | 32 | 8 | — | — | 74 | +7 | SIH |
| | | 9 | 13 | 14 | 13 | — | — | 32 | 1 | — | — | 82 | +6 | IH |
| 1-hydroxy-5,6-dichloro-2-(1,1,2,2-tetrafluoroethyl)-1H-imidazo(4,5-b)-pyridine | 200 | 12 | 10 | — | 13 | — | — | — | — | — | — | 35 | −3 | NGP |
| | | 12 | 9 | 0 | — | — | — | — | — | — | — | 21 | +4 | IH |
| | | 10 | 7 | — | — | 15 | — | — | — | — | — | 32 | −6 | IH |
| | | 12 | 9 | — | — | 19 | — | — | — | — | — | 40 | +1 | SIH |
| | | 13 | 12 | — | — | 25 | — | — | — | — | — | 50 | −7 | IH |
| " | 100 | 10 | 11 | — | — | 31 | 11 | 14 | 13 | 12 | — | 102 | +16 | NGP |
| | | 10 | 10 | — | — | 29 | 11 | 9 | 9 | 9 | — | 87 | +1 | NGP |
| | | 9 | 8 | — | — | 24 | 1 | — | — | — | — | 42 | +4 | IH |
| | | 10 | 10 | — | — | 36 | 14 | 13 | 12 | 1 | — | 96 | +3 | IH |
| | | 11 | 11 | — | — | 35 | 13 | 15 | 14 | 14 | — | 113 | +23 | NGP |
| 1-allyloxy-5,6-dichloro-2-(1,1,2,2-tetrafluoroethyl)-1H-imidazo(4,5-b)pyridine | 200 | 13 | 7 | — | 8 | — | — | — | — | — | — | 28 | −8 | IH |
| | | 12 | 7 | — | — | — | — | — | — | — | — | 19 | +2 | IH |
| | | 9 | 6 | — | — | — | — | — | — | — | — | 15 | +4 | IH |
| | | 12 | 9 | — | — | 19 | — | — | — | — | — | 40 | −4 | IH |
| | | 12 | 7 | 0 | — | — | — | — | — | — | — | 19 | +2 | IH |
| " | 100 | 12 | 12 | — | — 40$^w$ | 1 | — | — | — | — | — | 65 | 0 | SIH |
| | | 12 | 13 | — | — | 37 | 3 | — | — | — | — | 65 | +7 | NGP |
| | | 13 | 13 | — | — | 36 | — | — | — | — | — | 62 | +3 | NGP |
| | | 10 | 11 | — | — | 31 | 1 | — | — | — | — | 53 | +1 | IH |
| | | 9 | 9 | — | — | 28 | 2 | — | — | — | — | 48 | 0 | NGP |
| 1-benzyloxy-5,6-dichloro-2-(1,1,2,2-tetrafluoroethyl)-1H-imidazo(4,5-b)pyridine | 200 | 12 | 10 | — | 10 | — | — | — | — | — | — | 32 | −3 | SIH |
| | | 11 | 8 | — | 7 | — | — | — | — | — | — | 26 | +2 | SIH |
| | | 13 | 12 | — | — | 34 | — | — | — | — | — | 59 | −5 | IH |
| | | 11 | 11 | — | 8 | — | — | — | — | — | — | 30 | −2 | NGP |
| | | 12 | 9 | — | 8 | — | — | — | — | — | — | 29 | −1 | SIH |

TABLE I-continued

| Compound | Concentration of compound in diet | Grams of Feed Consumed per day of experiment | | | | | | | | | | Total feed consumed | Weight Change in grams | Necropsy Results |
|---|---|---|---|---|---|---|---|---|---|---|---|---|---|---|
| | | 1 | 2 | 3 | 4 | 5 | 6 | 7 | 8 | 9 | 10 | | | |
| " | 100 | 11 | 10 | — | — | 33 | 10 | 11 | 12 | 12 | — | 99 | +14 | NGP |
| | | 8 | 9 | — | — | 32 | 15 | 16 | 13 | 13 | — | 106 | +16 | NGP |
| | | 12 | 11 | — | — | 45 | 13 | 15 | 6 | — | — | 102 | +11 | IH |
| | | 7 | 7 | — | — | 28 | 12 | 12 | 12 | 11 | — | 89 | +4 | NGP |
| | | 10 | 12 | — | — | 36 | 15 | 11 | — | — | — | 84 | +3 | IH |
| 1-methoxy-5,6-dichloro-2-(1,1,2,2-tetrafluoroethyl)-1H-imidazo(4,5-b)-pyridine | 200 | 13 | 11 | — | — | 19 | — | — | — | — | — | 43 | +2 | IH |
| | | 8 | 8 | — | 9 | — | — | — | — | — | — | 25 | +1 | SIH |
| | | 11 | 9 | — | 7 | — | — | — | — | — | — | 27 | −5 | SIH |
| | | 11 | 11 | 9 | — | — | — | — | — | — | — | 31 | +4 | IH |
| | | 7 | 9 | — | 9 | — | — | — | — | — | — | 25 | +2 | IH |
| " | 100 | 12 | 11 | — | — | 35 | 14 | 14 | 2 | — | — | 88 | +6 | NGP |
| | | 11 | 12 | — | — | 39 | 15 | 14 | 13 | 14 | — | 118 | +24 | NGP |
| | | 12 | 11 | — | — | 43 | 16 | 17 | 17 | 15 | — | 131 | +24 | NGP |
| | | 17 | 17 | — | — | 62 | 21 | 25 | 21 | 16 | — | 179 | +50 | NGP |
| | | 12 | 15 | — | — | 43 | 13 | 12 | 1 | — | — | 96 | +10 | IH |
| 1-n-propoxy-5,6-dichloro-2-(1,1,2,2-tetrafluoroethyl)-1H-imidazo(4,5-b)-pyridine | 200 | 8 | 7 | 7 | 6 | — | — | — | — | — | — | 28 | −7 | IH |
| | | 10 | 8 | 9 | 2 | — | — | — | — | — | — | 29 | −7 | SIH |
| | | 10 | 8 | 8 | 1 | — | — | — | — | — | — | 27 | −1 | NGP |
| | | 11 | 9 | 9 | 3 | — | — | — | — | — | — | 32 | −7 | IH |
| | | 7 | 8 | 8 | — | — | — | — | — | — | — | 23 | −1 | NGP |
| " | 125 | 9 | 12 | 9 | 11 | — | 13 | — | — | — | — | 54 | +4 | NGP |
| | | 9 | 7 | 8 | 7 | 1 | — | — | — | — | — | 32 | −5 | IH |
| | | 11 | 11 | 11 | 11 | — | 11 | — | — | — | — | 55 | +4 | IH |
| | | 13w | 10 | 11 | 11 | — | — | 16 | — | — | — | 61 | +3 | IH |
| | | 5 | 11 | 10 | 9 | — | 9 | — | — | — | — | 44 | −3 | IH |
| 1-methoxy-5,6-dichloro-2-trifluoromethyl-1H-imidazo-(4,5-b)pyridine | 200 | 10 | 10 | 8 | 5 | 0 | — | — | — | — | — | 33 | −1 | IH |
| | | 10 | 11 | 9 | 8 | 0 | — | — | — | — | — | 38 | +2 | IH |
| | | 10 | 9 | 6 | 2 | — | — | — | — | — | — | 27 | −5 | IH |
| | | 7 | 6 | 7 | 5 | — | — | — | — | — | — | 25 | −12 | IH |
| | | 10 | 9 | 7 | 12 | 0 | — | — | — | — | — | 38 | −2 | IH |
| " | 125 | 10 | 11 | 11 | 10 | — | 8 | — | — | — | — | 50 | +4 | IH |
| | | 7 | 8 | 7 | 10 | — | — | 23 | 3 | — | — | 58 | −3 | IH |
| | | 10 | 10 | 11 | 10 | — | 10 | — | — | — | — | 51 | +6 | IH |
| | | 13w | 8 | 8 | 8 | — | — | 25 | 9 | 8 | 5 | 84 | −2 | NGP |
| | | 5 | 10 | 12 | 10 | — | — | 34 | 11 | 1 | — | 83 | +6 | NGP |
| 1-isopropoxy-5,6-dichloro-2-trifluoromethyl-1H-imidazo-(4,5-b)pyridine | 200 | 11 | 8 | 8 | 9 | — | 9 | — | — | — | — | 45 | −1 | IH |
| | | 7 | 6 | 4 | 5 | — | 6 | — | — | — | — | 28 | −4 | IH |
| | | 6 | 7 | 7 | 6 | — | 6 | — | — | — | — | 32 | −1 | SIH |
| | | 11 | 9 | 8 | 8 | — | 10 | — | — | — | — | 46 | 0 | NGP |
| | | 10 | 9 | 7 | 7 | 3 | — | — | — | — | — | 36 | −3 | IH |
| " | 125 | 10 | 11 | 12 | 11 | — | — | 40 | 21 | 11 | 0 | 116 | +16 | IH |
| | | 10 | 8 | 9 | 8 | — | — | 30 | 19 | 0 | — | 84 | +12 | NGP |
| | | 3 | 13 | 7 | 7 | — | — | 13 | — | — | — | 43 | −5 | IH |
| | | 9 | 6 | 7 | 7 | — | — | 17 | — | — | — | 46 | −3 | NGP |
| | | 11 | 11 | 11 | 9 | — | — | 22 | — | — | — | 64 | −3 | NGP |
| 1-methoxy-2,6-bis-(trifluoromethyl)-1H-imidazo(4,5-b)-pyridine | 200 | 11 | 9 | 11 | 10 | — | — | 22 | — | — | — | 63 | +9 | SIH |
| | | 11 | 9 | 10 | 8 | — | — | 27 | — | — | — | 65 | +2 | IH |
| | | 9 | 8 | 10 | 8 | — | — | 26 | 9 | 6 | — | 76 | +5 | IH |
| | | 9 | 8 | 9 | 6 | — | 11 | — | — | — | — | 43 | −2 | IH |
| | | 10 | 12 | 12 | 11 | — | 17 | — | — | — | — | 62 | +6 | IH |
| 1-methoxy-5-chloro-2-trifluoromethyl-1H-imidazo(4,5-b)pyridine | 800 | 7 | 4 | 3 | 1 | — | — | — | — | — | — | 15 | −11 | SIH |
| | | 5 | 4 | 3 | 5 | 0 | — | — | — | — | — | 17 | −11 | TH |
| | | 6 | 3 | 4 | 5 | — | 7 | — | — | — | — | 25 | −9 | SIH |
| | | 8 | 4 | 6 | 4 | — | — | 15 | 0 | — | — | 37 | −6 | NGP |
| | | 8 | 4 | 6 | 0 | — | — | — | — | — | — | 18 | −9 | NGP |
| 1-cinnamoyloxy-6-chloro-2-trifluoromethyl-1H-imidazo-(4,5-b)pyridine | 2000 | 7 | 3 | 4 | 6 | — | — | 18 | — | — | — | 38 | −12 | NGP |
| | | 6 | 7 | 7 | 4 | 3 | — | — | — | — | — | 27 | −13 | IH |
| | | 10 | 8 | 8 | 1 | — | — | — | — | — | — | 27 | −11 | IH |
| | | 8 | 4 | 7 | 9 | 0 | — | — | — | — | — | 28 | −11 | IH |
| | | 6 | 7 | 8 | 10 | — | — | 28 | 11 | 11 | 10 | 91 | −6 | NGP |
| " | 1000 | 11 | 10 | 11 | 14 | — | — | 9 | — | — | — | 55 | +14 | TH |
| | | 12 | 9 | 13w | 13 | — | — | 20 | 9 | 6 | 6 | 88 | −3 | TH |
| | | 10 | 10 | 13 | 12 | — | 20 | — | — | — | — | 65 | +16 | TH |
| | | 8 | 8 | 10 | 11 | — | — | 29 | 1 | — | — | 67 | +2 | SH, IH, TH |
| | | 8 | 6 | 9 | 9 | 5 | — | — | — | — | — | 37 | +8 | TH |
| 1-benzoyloxy-6-chloro-2-trifluoromethyl-1H-imidazo-(4,5-b)pyridine | 2000 | 8 | 5 | 7 | 0 | — | — | — | — | — | — | 20 | −10 | IH |
| | | 13w | 15w | 11 | 31w | — | — | 42 | — | — | — | 112 | −10 | NGP |
| | | 5 | 5 | 9 | 5 | — | — | — | — | — | — | 24 | −8 | IH |
| | | 9 | 7 | 9 | 10 | — | 17 | — | — | — | — | 52 | −8 | IH |
| | | 8 | 6 | 6 | 0 | — | — | — | — | — | — | 20 | −13 | IH |
| 6-chloro-2-(1,1,2,2- | 300 | 11 | 10 | 13 | 12 | — | — | 38 | 2 | — | — | 86 | +21 | TH |

TABLE I-continued

| Compound | Concentration of compound in diet | Grams of Feed Consumed per day of experiment | | | | | | | | | | Total feed consumed | Weight Change in grams | Necropsy Results |
|---|---|---|---|---|---|---|---|---|---|---|---|---|---|---|
| | | 1 | 2 | 3 | 4 | 5 | 6 | 7 | 8 | 9 | 10 | | | |
| tetrafluoroethyl)-1H-imidazo(4,5-b)pyridine | | 11 | 12 | 13 | 9 | 0 | — | — | — | — | — | 45 | +8 | TH |
| | | 9 | 11 | 13 | 2 | — | — | — | — | — | — | 35 | +10 | TH |
| | | 8 | 10 | 11 | 10 | — | — | — | — | — | — | 39 | +13 | TH |
| | | 11 | 8ⁱʳ | 9 | 10 | 4 | — | — | — | — | — | 42 | +10 | TH |
| " | 150 | 14 | 12 | 13 | 5 | — | — | 2 | — | — | — | 46 | +3 | TH |
| | | 10 | 12 | 13 | 15 | — | — | 13 | 1 | 1 | 6 | 71 | +10 | TH |
| | | 10 | 11 | 12 | 10 | 0 | — | — | — | — | — | 43 | +14 | TH, SIH |
| | | 11 | 12 | 12 | 8 | 1 | — | — | — | — | — | 44 | +15 | NH, IH, TH |
| | | 11ʷ | 11ⁱʳ | 10 | 10 | — | — | 32 | 9 | 7 | 8 | 98 | +18 | SH |
| 1-acetoxy-6-chloro-2-trifluoromethyl-1H-imidazo(4,5-b)-pyridine | 2000 | 6 | 7 | 10 | 11 | — | — | 37 | 9 | 8 | 5 | 93 | −15 | NGP |
| | | 7 | 5 | 9 | 6 | 3 | — | — | — | — | — | 30 | −8 | TH |
| | | 6 | 6 | 9 | 9 | — | — | 19 | — | — | — | 49 | −15 | IH |
| | | 5 | 5 | 6 | 8 | — | 9 | — | — | — | — | 33 | −5 | TH |
| | | 10 | 6 | 8 | 0 | — | — | — | — | — | — | 24 | −12 | IH |
| 1-pivaloyloxy-6-chloro-2-trifluoromethyl-1H-imidazo-(4,5-b)pyridine | 1500 | 7 | 8 | 8 | 10 | — | — | 33 | 8 | 8 | 4 | 86 | −14 | NH |
| | | 2 | 4 | 5 | 7 | — | — | 20 | 6 | 3 | — | 47 | −12 | TH |
| | | 7 | 7 | 10 | 10 | — | 15 | — | — | — | — | 49 | −12 | NH, IH |
| | | 9 | 7 | 8 | 0 | — | — | — | — | — | — | 24 | −10 | IH |
| " | | 7 | 6 | 7 | 6 | 0 | — | — | — | — | — | 26 | −6 | TH |
| | 750 | 11 | 10 | 10 | 12 | — | — | 41 | 15 | 12 | 11 | 122 | +27 | SH |
| | | 8 | 10 | 12 | 13 | — | — | 27 | — | — | — | 70 | +21 | TH |
| | | 11 | 11 | 10 | 13 | — | — | 26 | 10 | 10 | 0 | 91 | +9 | TH |
| | | 12 | 9 | 13 | 11 | 0 | — | — | — | — | — | 45 | −1 | TH, IH |
| | | 11 | 10 | 10 | 12 | — | — | 34 | 0 | — | — | 77 | +12 | NH, IH |
| 1-(methoxymethoxy)-6-chloro-2-trifluoromethyl-1H-imidazo-(4,5-b)pyridine | 700 | 10 | 7 | 9 | 11 | — | — | 38 | 12 | 11 | 8 | 106 | +13 | SH |
| | | 8 | 8 | 10 | 11 | 0 | — | — | — | — | — | 37 | +6 | TH |
| | | 11 | 7 | 11 | 12 | — | 20 | — | — | — | — | 61 | +5 | TH |
| | | 10 | 10 | 12 | 9 | 5 | — | — | — | — | — | 46 | +2 | TH |
| | | 7 | 10 | 10 | 9 | — | 10 | — | — | — | — | 46 | +5 | NH, IH |

EXAMPLE 29

1-Hydroxy-6-chloro-2-pentafluoroethyl-1H-imidazo(4,5-b)-pyridine was evaluated for prolongation of clotting time. The experiment was conducted in female rats (*Rattus norvegicus*, Sprague-Dawley strain) using a standard laboratory diet. A group of four control rats was fed the unmodified diet and another group of four rats was fed a treated diet, the standard laboratory diet modified by the incorporation therein of 0.06 percent of the 1-hydroxy-6-chloro-2-pentafluoroethyl-1H-imidazo(4,5-b)pyridine.

On the sixth day of feeding, a blood sample was taken from each rat and was analyzed for whole blood clotting time. The analysis was carried out on a BBL Fibrometer Precision Coagulation Timer, produced by BBL Fibrometer, a Division of Becton, Dickinson and Co., Canada, Ltd.; at Mississauga, Ontario. Two analyses were made of each sample. The results are reported in Table II

Table II

| Treatment | Animal Number | Whole Blood Clotting Time in Seconds |
|---|---|---|
| Control | 1 | 108 |
| | | 95 |
| " | 2 | 104 |
| | | 102 |
| " | 3 | 127 |
| | | 125 |
| " | 4 | 113 |
| | | 108 |
| 0.06 % of 1-hydroxy-6-chloro-2-pentafluoroethyl-1H-imidazo(4,5-b)pyridine | 1 | >600 |
| " | | >600 |
| " | 2 | >600 |
| | | >600 |
| " | 3 | died on day 5, no analysis |
| " | 4 | died on day 6, no analysis |

EXAMPLE 30–33

Representative compounds were evaluated for prothrombin time in standard laboratory male rats (Harlan albino strain) of weanling age. A standard laboratory animal diet was fed to one group of 5 rats to serve as a control; other groups of 5 rats received modified diets, each diet being the standard laboratory animal diet modified by the incorporation therein of 0.08 percent of the respective compound. Feeding was continued for five days, at which time a blood sample was taken from each rat and analyzed for prothrombin time. The analytical method was that of A. J. Quick, "The Determination of Prothrombin," 190 *Am. J. Med. Sci.* 501 (1935): and it was performed on the "Electra 600", a machine available from the Medical Laboratory Automation, Inc. The results are reported in Table III.

Table III

| Compound | Deaths | Range of Prothrombin Time in Sec. |
|---|---|---|
| none (untreated control) | none | 18.6–22.5 |
| 1-methoxy-6-chloro-2-trifluoromethyl-1H-imidazo(4,5-b)pyridine | none | 50.1–109.1 |
| 6-chloro-2-trifluoromethyl-1H-imidazo-(4,5-b)pyridine | 5, on day three | — |
| 1-methoxy-6-chloro-2-pentafluoroethyl-1H-imidazo(4,5-b)-pyridine | 3, on days 2–4 | 180–200 |
| 1-methylcarbamoyloxy-6-chloro-2-trifluoromethyl-1H-imidazo(4,5-b)-pyridine | none | 39.6–98.6 |

EXAMPLES 34–37

Additional evaluations of the effect of representative compounds of prothrombin time were conducted. The procedures were the same as those reported in Examples 30–33 except that the concentration of the respective compound was 0.02 percent. The results were reported in Table IV.

Table IV

| Compound | Deaths | Range of Prothrombin Time in Sec. |
|---|---|---|
| none (untreated control) | none | 20.1–22.0 |
| 1-methoxy-6-chloro-2-trifluoromethyl-1H-imidazo(4,5-b)pyridine | none | 19.5–27.5 |
| 6-chloro-2-trifluoromethyl-1H-imidazo(4,5-b)pyridine | none | 83.7–>246 |
| 1-methoxy-6-chloro-2-pentafluoroethyl-1H-imidazo(4,5-b)-pyridine | none | 53.1–90.5 |
| 1-methylcarbamoyloxy-6-chloro-2-trifluoromethyl-1H-imidazo(4,5-b)-pyridine | none | 17.6–22.1 |

EXAMPLES 38–39

Each of 1-methoxy-6-chloro-2-trifluoromethyl-1H-imidazo-(4,5-b)pyridine and 1-hydroxy-6-chloro-2-trifluoromethyl-1H-imidazo(4,5-b)pyridine was evaluated in coagulation studies in dogs (beagles weighing about 10 kilograms each). Two dogs were employed with each compound, one female and one male.

In the first part of the evaluation, a blood sample was taken from each dog prior to any treatment with the respective compound. The sample was citrated and centrifuged for 10–15 minutes to segregate the plasma, which was separated and quick frozen. The dogs were then treated: each dog received 40 mg./kg. of the respective compound on each of 3 successive days; administration was by the oral route. On the fourth day, blood samples were again taken and processed as described above. Throughout the test, the dogs were provided with adequate food and water and otherwise maintained under good conditions. The samples were subsequently thawed and analyzed for prothrombin time activated partial thromboplastin, thrombin clotting time, and fibrinogen levels. The first three analyses were conducted on a "Bioquest Fibrometer", produced by Baltimore Biological Division of Becton and Dickinson at Cockeysville, Maryland 21030, Fibrinogen levels were determined by the method of H. O. Bang, 9 Scand. J. Clin. Lab. Inves. 205 (1957). The results are reported in Table V. The results show that each of the compounds prolongs prothrombin time and that 1-methoxy-6-chloro-2-trifluoromethyl-1H-imidazo(4,5-b)pyridine prolongs activated partial thromboplastin time as well.

In the second part of the evaluation, a sample was taken from each of the same four dogs prior to any treatment (at the same time as the initial sample for the first part of the evaluation), and the samples were pooled and evaluated for the concentration of individual clotting factors, to serve as a control. Following the treatment described above, a sample was again taken from each dog and individually analyzed in the same manner. The control figure was considered as 100 percent and the scores for the treated dogs were reported as percent of the control figure. Analyses were by the following methods:

II F. Koller et al., 6 Acta Haem. 1 (1951).
V A. J. Quick, 13 J. Clin. Path. 457 (1960).
VII F. Bachman et al., 1 Thrombosis Diathes. Haemorrh. 169 (1957)
VIII R. D. Langdell et al., 41 J. Lab. Clin. Med. 637 (1953).
IX W. F. Stapp, 10 Scand. J. Clin. Lab. Inves. 169 1 (1958).
X Same as VII
XI S. I. Rapaport, 57 J. Lab. Clin. Med. 771 (1961).
XII O. D. Ratnoff in Thrombosis and Bleading Disorders, ed. by N. U. Bang et al. (G. Thieme, and Academic Press, N.Y., 1971), pages 214–221.

The results are reported in Table VI. These results show that each of the compounds suppresses those factors (II, VII, IX, and X) in the prothrombin family.

TABLE V

| Dog. No. | Plasma Sample | Prothrombin Time | Activated Partial Thromboplastin Time | Thrombin Clotting Time | Fibrinogen Levels (mg%) |
|---|---|---|---|---|---|
| 1 | Control | 8.6 secs. | 17.1 secs. | 12.3 secs. | 200 |
| 1 | After treatment with 1-methoxy-6-chloro-2-trifluoromethyl-1H-imidazo(4,5-b)pyridine | 12.2 secs. | 18.9 secs. | 10.5 secs. | 236 |
| 2 | Control | 5.7 secs. | 19.8 secs. | 12.4 secs. | 295 |
| 2 | After treatment with 1-methoxy-6-chloro-2-trifluoromethyl-1H-imidazo(4,5-b)pyridine | 12.9 secs. | 26.2 secs. | 13.9 secs. | 222 |
| 3 | Control | 8.9 secs. | 24.2 secs. | 12.6 secs. | 192 |
| 3 | After treatment with 1-hydroxy-6-chloro-2-trifluoromethyl-1H- | | | | |

TABLE V-continued

| Dog. No. | Plasma Sample | Prothrombin Time | | Activated Partial Thromboplastin Time | | Thrombin Clotting Time | | Fibrinogen Levels (mg%) |
|---|---|---|---|---|---|---|---|---|
|  | imidazo(4,5-b)pyridine | 9.9 | secs. | 22.9 | secs. | 12.2 | secs. | 223 |
| 4 | Control | 5.9 | secs. | 16.0 | secs. | 14.0 | secs. | 172 |
| 4 | After treatment with 1-hydroxy-6-chloro-2-trifluoromethyl-1H-imidazo(4,5-b)pyridine | 6.9 | secs. | 16.0 | secs. | 12.0 | secs. | 218 |

TABLE VI

| Treatment | Coagulation Factor (% of Control) | | | | | | | |
|---|---|---|---|---|---|---|---|---|
|  | Prothrombin (II) | Ac Globulin (V) | Proconvertin (VII) | AHG (VIII) | PTC (IX) | Stuart Factor (X) | PTA (XI) | Hageman Factor (XII) |
| 1-methoxy-6-chloro-2-trifluoromethyl-1H-imidazo(4,5-b)-pyridine | 39 | 100 | 9 | 124 | 26 | 4 | 224 | 25 |
| " | 39 | 100 | 14 | 122 | 35 | 6 | 200 | 43 |
| 1-hydroxy-6-chloro-2-trifluoromethyl-1H-imidazo(4,5-b)-pyridine | 70 | 100 | 11 | 94 | 45 | 11 | 128 | 37 |
| " | 70 | 100 | 20 | 100 | 66 | 25 | 140 | 18 |

EXAMPLE 40

A field trial was conducted to evaluate the efficacy of 1-methoxy-5,6-dichloro-2-heptafluoro-n-propyl-1H-imidazo(4,5-b)-pyridine. The trial was conducted in an area of waste ground covered by grass and brush and recently cut off, by construction activity, from a nearby abandoned stockyard. The trial area indicated the presence of a rat population; this was confirmed by supplying to the area a conventional pelleted hog feed. It was consumed steadily at the rate of 8 lbs./day, corresponding to a population of about 145 rats consuming an average of 25 g. of feed/day. After the conventional feed had been supplied for three weeks, the trial period began. The rat species was believed to be $Rattus\ norwegius$, and this was later confirmed upon recovery of the dead animals.

During the trial period, the conventional feed was replaced by an adequate supply of a modified feed, which was identical to the conventional feed except that it contained 100 ppm (0.01 percent) of 1-methoxy-5,6-dichloro-2-heptafluoro-n-propyl-1H-imidazo(4,5-b)pyridine.

Food consumption was estimated visually and was as follows, counting the initiation of the trial period as the first day:

| By day | Total Pounds of Feed Consumed |
|---|---|
| 4 | about 20–25 |
| 7 | about 45 |
| 10 | about 45 |
| 12 | about 49 |

As shown above, the rats intially consumed the modified feed at essentially the same rate as the conventional feed, indicating that there was no bait shyness. Food consumption after day 7 tapered off to essentially nothing.

Rat corpses were found in the trial area beginning on day 4. A total of 40 corpses was found. Of these, 31 were necropsied and uniformly showed internal hemorrhage, generally of the intestines.

In view of the difficulty in locating corpses, and the pattern of feed consumption, it was believed that there had been achieved an essentially complete eradication of rodents from the trial area.

I claim:

1. A method for reducing or eradicating a rodent population which comprises supplying to a locus frequented by said population an effective amount of an active agent which comprises at least one compound selected from the group consisting of those compounds of the formula

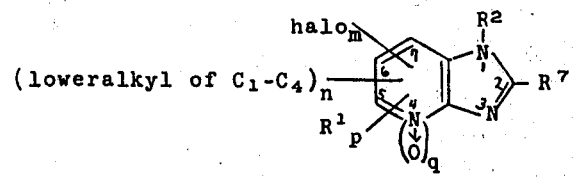

and the salts, with non-toxic cations, of those compounds wherein $R^2$ represents hydrogen or hydroxy; wherein $R^1$ represents
  1. —$CF_3$,
  2. —$CF_2Cl$, or
  3. —$CF_2H$;

$n$ represents an integer from 0 to 3; $q$ represents 0 or 1; each of $n$ and $p$ represents 0 or 1, subject to the limitations (1) that where $n$ is 1, the loweralkyl group so specified is at the 6-position; and (2) that the sum of $m$, $n$, and $p$ is an integer from 1 to 3;

$R^2$ represents
  1. hydrogen,
  2. hydroxy, or
  3. $OR^3$ where $R^3$ represents
     a. alkyl of $C_1$-$C_8$,
     b. (loweralkoxy of $C_1$-$C_4$)methyl,
     c. alkenyl of $C_2$-$C_8$,
     d. cycloalkyl of $C_5$-$C_6$,
     e. benzyl,
     f. phenethyl,
     g. alkanoyl of $C_2$-$C_{18}$,
     h. alkenoyl of $C_3$-$C_{18}$,
     i. carbamoyl of the formula

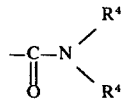

wherein one R⁴ represents phenyl, loweralkyl of $C_1$-$C_4$, or loweralkenyl of $C_2$-$C_4$, and the other R⁴ represents hydrogen, loweralkyl of $C_1$-$C_4$, or loweralkenyl of $C_2$-$C_4$, subject to the limitation that both R⁴ moieties taken together do not contain more than six carbon atoms;

j. radical of the formula

loweralkyl of $C_1$-$C_4$ or

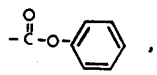

k. radical of the formula

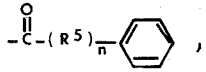

wherein R⁵ represents methylene, ethylene, or vinylene, and $n$ represents 0 or 1, l. —$SO_2$- R⁶ wherein R⁶ is loweralkyl as above defined, cycloalkyl of $C_5$-$C_6$, phenyl, benzyl, or phenyl bearing from 1–3 substituents, each of which is independently amino, nitro chloro, methyl, or methoxy;

and R⁷ represents 1. perfluoroalkyl of $C_1$-$C_7$,
  2. —$CF_2H$, or
  3. —$CF_2$—$CF_2H$.

2. The method of claim 1 wherein the active agent is supplied in a composition comprising an effective amount of the active agent and one or more suitable adjuvants.

3. The method of claim 2 wherein the active agent is 1-methoxy-6-chloro-2-heptofluoro-n-propl-1H-imidazo(4,5-b)-pyridine.

4. The method of claim 2 wherein the active agent is 1-methoxy-6-bromo-2-heptafluoro-n-propyl-1H-imidazo(4,5-b)pyridine.

5. The method of claim 2 wherein the active agent is 6-chloro-2-pentafluoroethyl-1H-imidazo(4,5-b)pyridine.

6. The method of claim 2 wherein the active agent is 1-methoxy-6-chloro-2-heptafluoroisopropyl-1H-imidazo(4,5-b)pyridine.

7. The method of claim 2 wherein the active agent is 5,6-dichloro-2-(1,1,2,2-tetrafluoroethyl)-1H-imidazo(4,5-b)pyridine.

8. The method of claim 2 wherein the active agent is 5,6-dichloro-2-heptafluoro-n-propyl-1H-imidazo(4,5-b)pyridine.

9. The method of claim 2 wherein the active agent is 1-methoxy-5,6-dichloro-2-heptafluoro-n-propyl-1H-imidazo(4,5-b)-pyridine.

10. The method of claim 2 wherein the active agent is 5,6-dichloro-2-pentafluoroethyl-1H-imidazo(4,5-b)pyridine.

11. The method of claim 2 wherein the active agent is 5,6-dichloro-2-trifluoromethyl-1H-imidazo(4,5-b)pyridine.

12. The method of claim 2 wherein the active agent is 1-hydroxy-5,6-dichloro-2-(1,1,2,2-tetrafluoroethyl)-1H-imidazo-(4,5-b)pyridine.

13. The method of claim 2 wherein the active agent is 1-methoxy-5,6-dichloro-2-(1,1,2,2-tetrafluoroethyl)-1N-imidazo-(4,5-b)pyridine.

14. The method of claim 2 wherein the active agent is 5,6,7-trichloro-2-heptafluoro-n-propyl-1H-imidazo(4,5-b)pyridine.

15. The method of claim 2 wherein the active agent is 1-methoxy-5,6,7-trichloro-2-trifluoromethyl-1H-imidazo(4,5-b)-pyridine.

16. The method of claim 2 wherein the active agent is 5,6,7-trichloro-2-(1,1,2,2-tetrafluoroethyl)-1H-imidazo(4,5-b)pyridine.

* * * * *

UNITED STATES PATENT AND TRADEMARK OFFICE
CERTIFICATE OF CORRECTION

PATENT NO. : 3,941,882
DATED : March 2, 1976
INVENTOR(S) : George O. P. O'Doherty It is certified that error appears in the above-identified patent and that said Letters Patent are hereby corrected as shown below:

Column 1, line 9, "NO." should be -- No. --; line 60, "lower" should be -- other --; and lines 66-70, "loweralkyl of $C_1-C_4$" should be moved to be on the same line as $-\overset{\overset{O}{\|}}{C}-O-$, so that the text would read -- $\overset{\overset{O}{\|}}{C}-O-$loweralkyl of $C_1-C_4$ --.

Column 5, line 5, "ln" should be -- 1-n --; and line 15, "benzyloxy" should be --benzoyloxy--.

Column 8, line 36, "Representative compounds were evaluated for rodenticidal effect in rats" is not a heading, but the beginning of a paragraph.

Column 18, line 44, the "I" at the end of the line should be deleted.

Column 19, line 60, "intially" should be --initially--.

Column 20, Claim 1, line 51, "n" should be --m--.

Column 21, Claim 1, lines 15-20, "loweralkyl of $C_1-C_4$" should be moved to be on the same line as $-\overset{\overset{O}{\|}}{C}-O-$, so that the text would read --$\overset{\overset{O}{\|}}{C}-O-$loweralkyl of $C_1-C_4$ --;

line 34, insert a comma between "nitro" and "chloro"; and lines 37-39 should be indented to the same degree.

UNITED STATES PATENT AND TRADEMARK OFFICE
CERTIFICATE OF CORRECTION

PATENT NO. : 3,941,882
DATED : March 2, 1976
INVENTOR(S) : George O. P. O'Doherty It is certified that error appears in the above-identified patent and that said Letters Patent are hereby corrected as shown below:

Column 22, line 2, of Claim 3, "heptofluoro" should be --heptafluoro-- and "propl" should be --propyl--; and Claim 13, line 34, "1N" should be --1H--.

Signed and Sealed this second Day of August 1977

[SEAL]

Attest:

RUTH C. MASON
Attesting Officer

C. MARSHALL DANN
Commissioner of Patents and Trademarks